United States Patent
Bendorf et al.

(10) Patent No.: US 8,580,329 B2
(45) Date of Patent: Nov. 12, 2013

(54) DRY-MILL ETHANOL PLANT EXTRACTION ENHANCEMENT

(75) Inventors: Peter Bendorf, Berresford, SD (US); Dan Sonnek, Lake Crystal, MN (US)

(73) Assignees: Daniel W. Sonnek, Utica, SD (US); Gregory W. Loest, Utica, SD (US)

( * ) Notice: Subject to any disclaimer, the term of this patent is extended or adjusted under 35 U.S.C. 154(b) by 755 days.

(21) Appl. No.: 12/350,600

(22) Filed: Jan. 8, 2009

(65) Prior Publication Data

US 2009/0181153 A1  Jul. 16, 2009

Related U.S. Application Data

(60) Provisional application No. 61/019,720, filed on Jan. 8, 2008.

(51) Int. Cl.
| | |
|---|---|
| *A23L 1/28* | (2006.01) |
| *A23L 1/00* | (2006.01) |
| *C12P 21/06* | (2006.01) |
| *C12C 1/00* | (2006.01) |

(52) U.S. Cl.
USPC ............. 426/655; 426/430; 435/68.1; 435/93

(58) Field of Classification Search
USPC .................................. 426/11, 15, 16, 29, 655
See application file for complete search history.

(56) References Cited

U.S. PATENT DOCUMENTS

| | | | |
|---|---|---|---|
| 3,452,669 A | * | 7/1969 | Schaus ............................ 99/276 |
| 4,448,881 A | * | 5/1984 | Muller et al. .................. 435/162 |
| 6,217,664 B1 | | 4/2001 | Baniel |
| 2004/0187863 A1 | | 9/2004 | Langhauser |
| 2005/0009133 A1 | * | 1/2005 | Johnston et al. ................. 435/35 |
| 2006/0127999 A1 | | 6/2006 | Verser et al. |
| 2007/0037993 A1 | * | 2/2007 | Cheryan ............................ 554/8 |
| 2008/0003654 A1 | | 1/2008 | Hirl |

FOREIGN PATENT DOCUMENTS

CA  1211398 A  *  9/1986

* cited by examiner

*Primary Examiner* — Humera Sheikh
*Assistant Examiner* — Subbalakshmi Prakash
(74) *Attorney, Agent, or Firm* — Barbara A. Wrigley; Oppenheimer Wolff & Donnelly LLP

(57) ABSTRACT

In a liquid stream capture process for extracting various components in a dry mill ethanol process, a converted mash is separated into sugars/carbohydrates and corn residue by rinsing the converted mash with a dilute solvent stream and, after the sugars/carbohydrates have been separated, oils and proteins are extracted from the corn residue by rinsing the corn residue with a concentrated solvent stream. The dilute solvent stream is a mixture of ethanol and water, and the concentrated solvent stream is pure ethanol.

10 Claims, 2 Drawing Sheets

DRY-MILL ETHANOL PLANT EXTRACTION ENHANCEMENT

CROSS REFERENCE TO RELATED APPLICATION

This application claims priority from provisional application Ser. No. 60/019,720, filed Jan. 8, 2008.

BACKGROUND AND SUMMARY OF THE INVENTION

Ethanol can be produced through fermentation and distillation of starches found in feedstock crops such as corn, potatoes and sugar cane. Conventional processes for producing ethanol include dry milling and wet milling. A feature of the dry milling process is that the feedstock is processed without first separating it into its component parts. In a conventional dry milling production process, the starch portion of the crop is used to produce the ethanol while the remaining nutrients, including proteins, oils, minerals and vitamins, are typically concentrated into distillers grain, which is a valuable feed for livestock.

In dry milling, the entire starchy grain, commonly corn, is first ground into flour, which is then mixed with water to form a mash, heated to reduce bacteria levels prior to fermentation, and cooled. Enzymes are added to the mash to convert the starches to sugars. It may be advantageous to add enzymes during the mash-forming step in order to decrease the viscosity of the gelatinized starch, which facilitates ease of handling. The mash is transferred to reaction vessels where the starch is converted by addition of saccharifying enzymes to fermentable simple sugars such as sucrose, glucose and/or maltose. During saccharification, the mixture is preferably maintained at a temperature from about 100° F. to 110° F., more preferably about 105° F. Ammonia may be added to control the pH and as a nutrient for the subsequently added yeast.

The mixture of corn residue, sugar and water is next transferred to fermenters where yeast is added, which initiates the conversion of the sugars to ethanol and carbon dioxide gas. During the fermentation process, the mash is typically agitated and cooled in order to activate the yeast, and the carbon dioxide gas released during fermentation can be captured and used for carbonating beverages or for the manufacture of dry ice. After fermentation, the resulting beer is transferred to distillation columns where ethanol is separated from the remaining stillage.

The stillage, which includes both dissolved and suspended solids, is typically sent through a series of centrifuges and evaporators and then to a rotary dryer to reduce moisture. Prior to drying, the separated solids are referred to as the wet cake, while the output of the drying stage is a co-product called distillers dried grains (DDG).

The solubles are typically concentrated by evaporation. Corn condensed distillers solubles (CDS) is a term generally used to refer to evaporated co-products of the dry milling. In a conventional dry milling plant, most of the CDS are added to the dried grains, but some are available as a liquid feed ingredient. The solubles are an excellent source of vitamins and minerals, including phosphorus and potassium. CDS can be dried to about 5 wt. % moisture and marketed, but generally the water content is between about 50-75 wt. %.

The condensed distillers solubles (CDS) can be dried together with the wet cake to produce distillers dried grains with solubles (DDGS), which are recovered in the distillery and contain all the nutrients from the incoming corn except the starch.

Following fermentation and separation of the ethanol, feedstock oils (e.g., corn oil) can be extracted from the stillage. However, because the stillage is processed through the relatively high temperatures associated with fermentation and distillation, the oils typically are thermally degraded prior to extraction. The thermal degradation of the oils reduces their value.

In addition to the problem of thermal degradation, conventional processes for separating feedstock oils from the post-fermentation stillage typically use hexane-based solvents to facilitate the extraction. Hexane extraction plants are expensive to build, run, and maintain, however, due to the explosion hazard potential and the human and environmental safety issues and regulations.

In view of the foregoing, one object of the invention is to increase the efficiency of the dry milling fermentation process as well as the value output of the fermentation residuals, including the distillers grain and extractable oils.

Applicants' inventive liquid stream capture processes for extracting various components in a dry mill ethanol process achieve this and other objects and advantages of the invention. The liquid stream capture processes can be used to extract converted carbohydrates and sugars from a feedstock mash and, subsequently, to extract the feedstock oils and proteins from the residual solids.

According to one aspect of the invention, the corn residue, sugar and water mixture that is obtained by combining enzymes with the mash is rinsed with a dilute solvent stream in a bifurcating step in order to separate the sugars from the feedstock solids. According to a preferred embodiment, the dilute solvent stream comprises 2% ethanol and 98% water. The solute (sugars and water) can be transferred to fermenters.

According to a further aspect of the invention, after the bifurcating step, a concentrated solvent stream is used in conjunction with a mechanical extractor (such as, for example, a centrifuge) to produce a washout of miscella from the feedstock solids (corn residue). Specifically, after the sugars have been separated from the feedstock solids, the concentrated solvent separates the miscella (water, oils and proteins) from the solids. According to a preferred embodiment, the concentrated solvent stream comprises 100% ethanol.

After extraction of the miscella, adsorbed solvent can be removed from the solids, and the solids can be dried. A preferred apparatus for desorbing solvent from the residual solids is a desolventizer/toaster/dryer/cooler (DTDC) apparatus. Preferably, the recovered solvent is dried and recycled to wash out additional miscella.

In a separate step, the miscella can be separated into its constituent parts (water, oils and proteins) using, for example, fractional evaporation or other thermal processing. Retained solvent that is mixed with the miscella can also be separated using fractional evaporation.

Thus, the inventive method can be used to deliver a stream of sugars and water to a dry mill fermentation process and, after the sugars have been separated from the solids, to further extract useful miscella from the solids. Advantageously, the sugar/water stream is substantially free of suspended solids. By delivering a suspended solids free stream of sugars and water to the fermentation process, the subsequent isolation and purification of the product ethanol is greatly simplified.

Moreover, by extracting the miscella from pre-fermentation solids, the oils obtained are not thermally degraded prior to their extraction.

Other objects, advantages and novel features of the present invention will become apparent from the following detailed description of the invention when considered in conjunction with the accompanying drawings.

DETAILED DESCRIPTION OF THE DRAWINGS

Various embodiments according to the present invention are explained below with reference to FIG. 1, which is a flowchart of a known dry mill process, and FIG. 2, which illustrates an enhanced ethanol plant extraction method according to the present invention.

Figure 1:
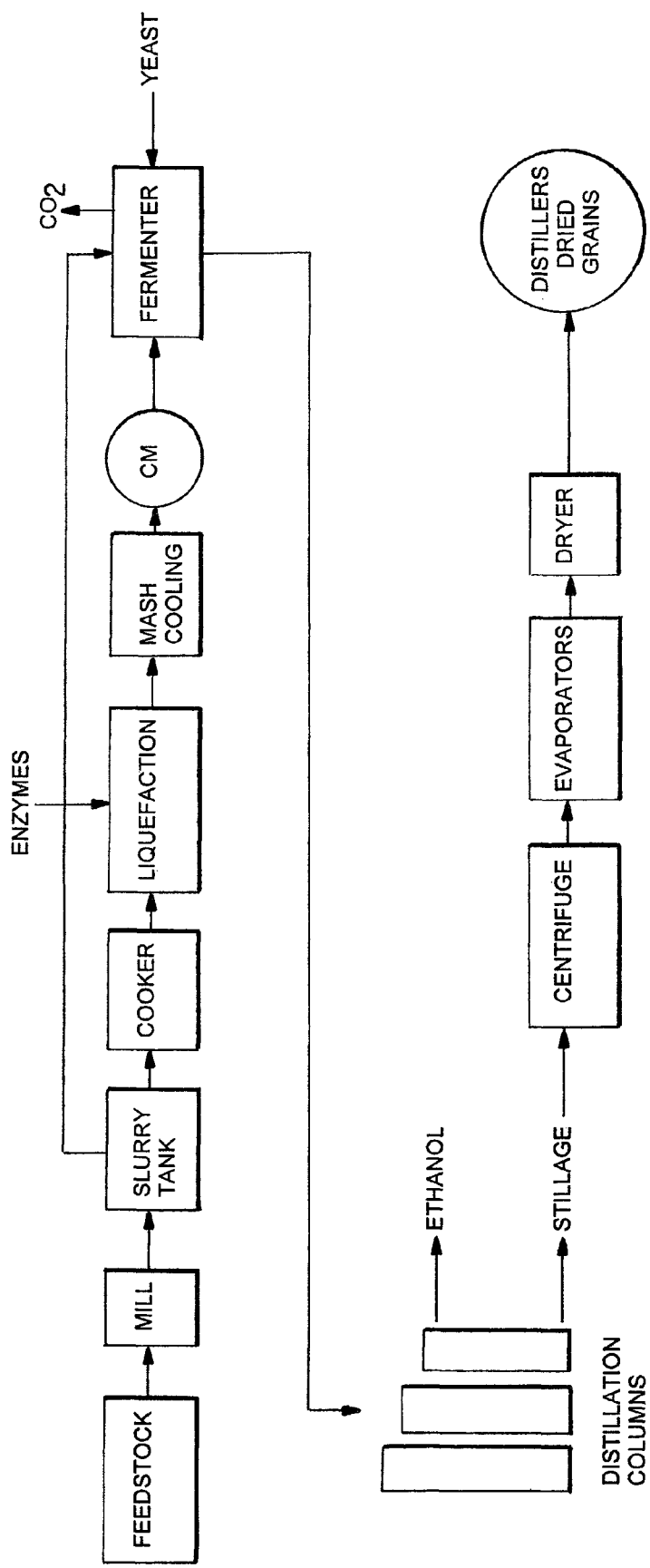
FIG. 1 is a flow chart showing a conventional dry milling process.

A conventional dry milling process is shown schematically in FIG. 1 and, as explained above, comprises the steps of milling or grinding, mash formation, cooking, liquefaction, and cooling. After liquefaction (saccharification), the converted mash CM comprises corn residue, sugars and water.

Figure 2:
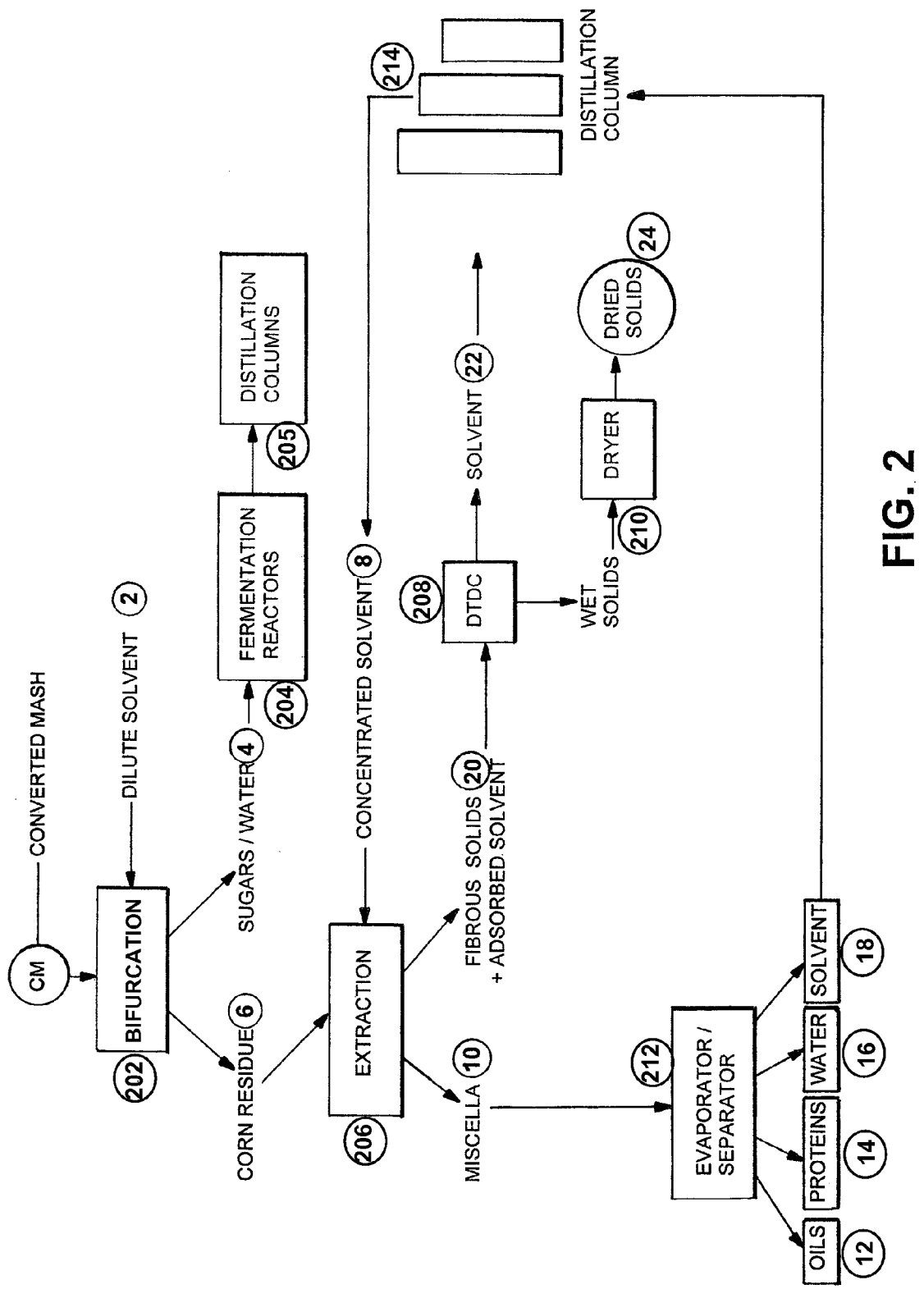
FIG. 2 is a flow chart showing the liquid stream capture processes according to various embodiments of the invention.

In contrast to the prior art, as shown in FIG. 2, in the process according to the invention, the converted mash CM, which may comprise 5-10 wt. % dissolved solids and 20-30 wt. % suspended solids (balance liquid), is cooled and, according to a first embodiment of the invention, rinsed with a dilute solvent stream 2. In this step 202, the dilute solvent stream 2 dissolves the sugars 4 in the converted mash CM and separates (bifurcates) the sugars 4 from the corn residue 6.

The dilute solvent stream 2 preferably comprises a mixture of ethanol and water. Ethanol diluted with up to 10% water (e.g., 1, 2, 4, 8 or 10% water) can be used. A particularly preferred dilute solvent stream 2 is a mixture of 2% ethanol and 98% water.

The foregoing bifurcation step 202, which separates sugars 4 from the corn residue 6, can be performed using a mechanical extractor apparatus or a centrifuge (the use of a centrifuge will cause a separation based on the density gradient of the constituents of the converted mash CM). A suitable mechanical extractor apparatus is marketed by Crown Iron Works Company (Minneapolis, Minn.). With such an apparatus, the converted mash CM is fed onto a porous grating and is raked over the grating by a plurality of paddles while a solvent spraying system sprays the converted mash with the dilute solvent 2. The grating operates as a filter: that is, the solvent and extractables (sugars) pass through the grating to a catch basin below, while the grating traps a majority of the solids.

According to one representative embodiment, the temperature of the converted mash CM that is fed onto the extractor grating is between about 175-185° F. (e.g., about 180° F.), while the temperature of the dilute solvent 2 is about 100° F. The step of bifurcating the converted mash can be run as a continuous process or as a batch process.

Having been separated from the corn residue 6, the sugars and carbohydrates can be fed to fermentation reactors 204 where yeasts are added and the fermentable sugars are converted to carbon dioxide and alcohol. The carbon dioxide by-product of the fermentation reaction can be separated, and the remaining liquid can be fed to a recovery system comprising distillation and stripping columns 205. Finally, the ethanol can be directed to molecular sieves where residual water is removed.

In a notable aspect of the first embodiment, the stream of sugars, carbohydrates and water that is delivered to the fermentation reactors 204 is substantially free of suspended solids. That is, while the sugar stream 4 may comprise dissolved solids, a majority of the suspended solids are separated from the sugars during the bifurcation step.

Referring to FIG. 2, after the sugars and carbohydrates have been extracted, the corn residue 6 can, in turn, be subjected to an extraction step 206 according to a second embodiment of the invention. With the sugars having been previously separated from the converted mash CM using a dilute solvent stream 2, miscella 10 are separated from the corn residue 6 by rinsing the corn residue 6 with a concentrated solvent stream 8. According to the second embodiment, a preferred concentrated solvent is 100% ethanol.

The extraction step 206 according to the second embodiment can be carried out using a mechanical extractor apparatus as described above. A preferred temperature of the corn residue during the extraction step ranges from about 90° F. to 110° F., more preferably from about 95° F. to 105° F.

The miscella 10 comprises oils 12, proteins 14, water 16, and solvent 18. The extraction of the miscella 10 from the corn residue 6 yields a fibrous solid byproduct 20. After the extraction step 206, the respective byproducts (miscella 10 and fibrous solids 20) can be processed further.

As illustrated in FIG. 2, the fibrous solids 20 can be run first through a desolventizer/toaster/drier/cooler (DTDC) apparatus 208 in order to remove any adsorbed solvent 22, and then through a drier 210 to produce dried solids 24. The recovered solvent 22 can be reintroduced into the spraying system of the mechanical extractor.

In a separate step, the constituents of the miscella 10 (oils, proteins, water and solvent) can be separated from each other in an evaporation/separation step 212. The evaporation/separation preferably comprises heating the miscella at a predetermined temperature and pressure.

The protein component 14, for example, can be precipitated from the other constituents of the miscella by heating. By heating the miscella, the proteins undergo denaturation and a concomitant loss of solubility. According to one step, proteins can be separated from the miscella by heating the miscella at atmospheric pressure to a first temperature between about 120-150° F. (e.g., about 135° F.). Alternatively, the proteins can be precipitated from the miscella without undergoing denaturation by heating the miscella to a second temperature under reduced pressure, and adjusting the pH to a range of 9.0-9.8. Preferably, the second temperature is less than the first temperature. For example, the proteins can be precipitated from the miscella by heating the miscella to a temperature between about 120 and 130° F. (e.g., 125° F. or thereabout) at a pressure of about 18 inches of vacuum.

Depending on the moisture content of the corn and other processing variables, the solvent may absorb water during the extraction, evaporation and/or separation steps. In order for the solvent to retain its effectiveness for extracting miscella, recaptured solvent is preferably dried prior to its reintroduction into the process. Drying of the solvent (ethanol) can be done, for example, using a distillation column 214. As with solvent 22 recovered pursuant to the extraction step 206, solvent 18 recovered from the evaporation/separation step 212 can be returned to the mechanical extractor.

As can be appreciated with reference to FIG. 2, the invention includes a first embodiment whereby the converted mash CM is separated into sugars/carbohydrates and corn residue using a dilute solvent stream, and a second embodiment whereby oils and proteins are extracted from the corn residue using a concentrated solvent stream.

As noted above, in a conventional dry milling process, prior to fermentation/distillation the sugars are not separated from the oil-bearing grains, and both the sugars and the grains are processed through fermentation and distillation where the oil-bearing grains are heated to temperatures effective to thermally degrade the oils. During distillation, for example, temperatures are typically greater than 200° F. (e.g., around 230° F. or 260° F.).

In contrast to conventional oil extraction methods where the oil is separated from post-distillation grains, according to a particularly advantageous aspect of the present invention, the oils and proteins are extracted from the corn residue, which is obtained from the bifurcating of the converted mash.

Having been separated from the fermentable sugars, the oil-bearing corn residue 6 is not heated during the fermentation 204 and distillation 205 steps and thus the oil 12 is not thermally degraded. The corn residue 6 is preferably not heated to a temperature greater than 200° F. prior to extraction of the oils. As a result, the oil (e.g., corn oil) obtained from the bifurcating 202, extraction 206, and evaporation/separation steps 212 is a high-quality, non-degraded, edible oil that can be marketed neat or blended with other ingredients.

The foregoing disclosure, including the drawings, has been set forth merely to illustrate the invention and is not intended to be limiting. Since modifications, combinations and subcombinations of the disclosed embodiments incorporating the spirit and substance of the invention may occur to persons skilled in the art, the invention should be construed to include everything within the scope of the appended claims and equivalents thereof.

What is claimed is:

1. A method of producing an oil that has not been thermally degraded from a converted mash in a dry mill ethanol production facility, said method comprising:
    (a) milling feedstock grains to produce flour;
    (b) adding water to the flour to form a mash;
    (c) adding enzymes to the mash to form a converted mash;
    (d) rinsing the converted mash with a dilute solvent stream consisting essentially of from 2% to 10% ethanol and from 90% to 98% water to separate a water and sugar component from a solid residue;
    (e) rinsing only the solid residue with 100% ethanol at a temperature of from about 90 degrees F. to about 110 degrees F. to extract a miscella and a fibrous solids component; and
    (f) precipitating protein from the miscella by passing the miscella through an evaporator/separator while heating said miscella at a temperature and pressure selected from 120 degrees F. to 150 degrees F. at atmospheric pressure or 120 degrees F. to 130 degrees F. at about 18 inches of vacuum,
wherein an oil that is not thermally degraded is produced from steps (a) through (f).

2. The method of claim 1, wherein the feedstock grains comprise whole kernel corn or flaked corn.

3. The method of claim 1, wherein the dilute solvent stream consists essentially of 2% ethanol and 98% water.

4. The method of claim 1, wherein the temperature of the dilute solvent stream is about 100° F.

5. The method of claim 1, wherein the step of rinsing the converted mash further comprises:
    feeding the converted mash onto a porous grating of a mechanical extractor apparatus; and
    raking the converted mash over the grating;
    wherein the rinsing comprises spraying the converted mash with said dilute solvent stream using a solvent spraying system.

6. The method of claim 5, wherein the temperature of the converted mash fed onto the porous grating is between about 175° F. and 185° F.

7. The method of claim 5, wherein the temperature of the dilute solvent stream is about 100° F.

8. The method of claim 5, wherein the temperature of the converted mash fed onto the porous grating is between about 90° F. and 110° F.

9. A method for extracting oil that has not been thermally degraded from a converted mash, said method comprising:
    first rinsing a feedstock grain mash with a dilute solvent stream consisting essentially of from 2 to 10% ethanol and from 90 to 98% water to separate water and sugars from feedstock grain solids;
    after the grain solids are separated from the water and sugars, rinsing only the solids with a concentrated solvent stream of 100% ethanol at a temperature of from about 90 degrees F. to about 110 degrees F. to separate extractable solute from the solids;
    heating the extractable solute to a predetermined temperature and pressure selected from a temperature of about 135 degrees F. at atmospheric pressure or a temperature of about 125 degrees F. at about 18 inches of vacuum to separate oils from the extractable solute; and
    producing an oil from the extractable solute that has not been thermally degraded.

10. A method for producing an oil that has not been thermally degraded from a converted mash in a dry mill ethanol production facility without affecting the sugars in the fluid streams, said method comprising:
    milling feedstock grains to produce flour;
    adding water to the flour to form a mash;
    adding enzymes to the mash to convert starches in the feedstock grains to sugars to form a converted mash comprising the water, the sugars, and feedstock grain solids;
    rinsing the converted mash with a mixture consisting essentially of from 2 to 10% ethanol and from 90 to 98% water to separate the water and the sugars from feedstock grain solids to form a solid residue;
    extracting miscella from the solid residue by rinsing the solid residue with a concentrated solvent stream of 100% ethanol at a temperature of from about 90 degrees F. to about 110 degrees F.;
    separating oils and proteins from the miscella by heating the miscella to a predetermined temperature and pressure selected from a temperature of about 135 degrees F. at atmospheric pressure or a temperature of about 125 degrees F. at about 18 inches of vacuum; and
    producing an oil that has not been thermally degraded from the miscella.

* * * * *